United States Patent [19]

Konishi et al.

[11] Patent Number: 5,079,148
[45] Date of Patent: Jan. 7, 1992

[54] PEPTIDE ANTIBIOTICS

[75] Inventors: Masataka Konishi, Kawasaki; Koji Tomita, Kami-yhoga; Masahisa Oka, Yokohama; Ken-ichi Numata, Tokyo, all of Japan

[73] Assignee: Bristol-Myers Squibb Company, New York, N.Y.

[21] Appl. No.: 579,453

[22] Filed: Sep. 7, 1990

Related U.S. Application Data

[60] Division of Ser. No. 414,357, Sep. 29, 1989, Pat. No. 5,025,023, which is a division of Ser. No. 309,527, Feb. 13, 1989, Pat. No. 4,898,940, which is a division of Ser. No. 51,433, May 19, 1987, Pat. No. 4,833,076, which is a division of Ser. No. 855,649, Apr. 25, 1986, Pat. No. 4,692,510, which is a continuation-in-part of Ser. No. 771,090, Apr. 25, 1986, abandoned.

[51] Int. Cl.$^5$ .................. C12P 21/06; C12P 17/16
[52] U.S. Cl. .................. 435/68.1; 435/71.3; 435/106; 435/121
[58] Field of Search .............. 435/68.1, 73.1, 121

[56] References Cited

U.S. PATENT DOCUMENTS

| | | | |
|---|---|---|---|
| 4,293,491 | 10/1981 | Debono | 435/68.1 |
| 4,299,762 | 11/1989 | Abbott et al. | 435/68.1 X |
| 4,524,135 | 6/1985 | Abbott et al. | 435/68.1 |
| 4,742,047 | 5/1988 | Oka et al. | 514/11 |
| 4,916,063 | 4/1990 | Oka et al. | 435/121 X |

*Primary Examiner*—Carolyn Elmore
*Attorney, Agent, or Firm*—David M. Morse

[57] ABSTRACT

Novel peptides of the formula

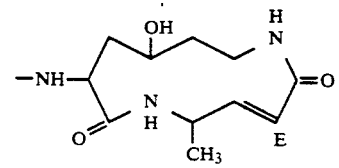

wherein R is $CH_3-(CH_2)_6$, $CH_3-(CH_2)_4-CH=CH-(CH_2)_2$ and $CH_3(CH_2)_8$ having antibiotic and antitumor activity are prepared by cultivation of the novel microorganism *Polyangium brachysporum*. Enzymatic hydrolysis of those peptides gives other peptides useful as intermediates in the preparation of peptides having activity as antibiotics and/or antitumor agents.

2 Claims, 5 Drawing Sheets

PEPTIDE ANTIBIOTICS

CROSS-REFERENCE TO RELATED APPLICATION

This application is a division of co-pending application Ser. No. 414,357, filed Sep. 29, 1989, issued as U.S. Pat. No. 5,025,023 on Jun. 8, 1991 which was a division of Ser. No. 309,527 filed Feb. 13, 1989 issued as U.S. Pat. No. 4,898,940 on Feb. 6, 1991 which was a division of Ser. No. 051,433 filed May 19, 1987, issued as Pat. No. 4,833,076 on May 23, 1989, which was a division of Ser. No. 855,649 filed Apr. 25, 1986, issued as Pat. No. 4,692,510 on Apr. 25, 1986, which was a CIP of Ser. No. 771,090 filed Apr. 25, 1986, now abandoned.

BACKGROUND O THE INVENTION

This invention relates to novel peptide antibiotics and to their use as antimicrobial and antitumor agents. The present invention also relates to methods for the preparation of these antibiotics, intermediates therefor and to the novel microorganism used in their preparation by fermentation.

Various microorganisms have been isolated from soil s, cultured in a synthetic medium and found to elaborate products having antibiotic activity. We have isolated a novel bacterium species, K481-B101, from a soil sample collected near the Parthenon in athens, Greece, and discovered it to produce a mixture of peptides having antibioticactivity.

It is a primary object of this invention to provide novel peptide antibiotics particularly useful as antifungal and antitumor agents.

It is also an object of the present invention to provide convenient methods for the preparation of these antibiotics. And, it is a further object of the invention to provide pharmaceutical compositions containing those antibiotics.

SUMMARY OF THE INVENTION

In accordance with the aforementioned objects, the present invention is a compound of the formula wherein R is $CH_3-(CH_2)_6$, $CH_3-(CH_2)_4-CH=CH(CH_2)_2$ or $CH_3-(CH_2)_8$.

In a further aspect, the invention includes pharmaceutical compositions comprising an amount of those compounds, singly or bination, effective as an antifungal and/or antitumor agent, together with a pharmaceutically acceptable carrier.

In its preparative aspect, the present invention is a "method for the preparation of a compound of the formula wherein R is $CH_3-(CH_2)_6$, $CH_3-(CH_2)_4CH=CH-(CH_2)_2$ or $CH_3-(CH_2)_8$, which comprises culturing Polyangium brachysporum sp. nov. in a medium containing an assimilable source of carbon and nitrogen under aerobic conditions, separating the mycelia produced and recovering the compound from the nutrient medium.

In a further composition aspect, the present invention includes the compounds and useful as intermediates in the preparation of the compounds of the invention, and methods for the preparation of those intermediate compounds.

BRIEF DESCRIPTION O THE DRAWINGS

FIGS. 1, 2 and 3 are the IR spectra of Bu-2867T A, B and C, respectively.

FIGS. 4 and 5 are the H-NMR and $^{13}$C-NMR spectra of Bu-2867T A.

DERAILED DESCRIPTION

The morphological, cultural and physiological characterization of K481-B101 was made by the methods described by McCurdy, Jr. H.D.: Studies on the Taxonomy of the Mvxobacterales. II, Polyangium and the demise of. the Sorangiaceae. Intle J. Syst. Bacteriol. 20: 283-296, 1970; Reichenbach, H.: Nannocystis exedens gen. nov., sp. nov., a new myxobacterium of the family Sorangiaceae. Arch Mikrobiol. 70: 119-138, 1970; Christensen, P. and F. D. Cook: Lysobacter, a new Genus of non-fruiting, gliding bacteria with a high base ratio. Intl. J. Syst. Bacteriol. 28: 367-393, 1978; and Christensen, P.: Synonymy of Flavobacterium ectinovorum Dorey with Cytophaga johnsonae Stanier. Intl. J. Syst. Bacteriol, 27: 122-132, 1977. Maintanance and purification was by the procedures described by Peterson, J.E.: Isolation, cultivation and maintenance of the myxobacteria. Methods in Microbiology 3B:

185-210, 1969. Edit. J. R. Norris & D. W. Ribbons. Academic Press (London and New York); and Reichenbach, H & M. Dworkin: The Order Mixobacterales. The Prokaryotes. Volume : 328-355, 1981. Edit. M. P. tarr et al. Springer-Verlag (Berlin, Heidelberg and N.Y.) The taxonomic position was determined according to the descriptions in Bergey's Manual, 8the Ed., 1974 and "The Prokaryotes, Vol. I".

MORPHOLOGY:

Casitone-Mg++agar, chitin agar, yeast cell agar and rabbit dung pellet-water agar were used for the mcrphological study. K-481 B101 is a Gram-negative, non-flagellate bacterium. The vegetative cells are cylindrical (0.6–0.8 by 2–10 micrometers) with blunt rounded ends. The vegetative cells show flexible and slow gliding movements on moist surface of agar medium or soft agar medium. Myxospores differ clearly from vegetative cells, are oval or spherical, 0.6–0.8 by 0.6–1.5 micrometers, non-refractile or refractile, and occasionally pair. K481-B101 forms on most descriptive agar media sessile sporangia enveloping myxospores. The sporangia are oval, spherical or pillow-like, fairly variable in size, 12×20 to 80×120 micrometers, often bounded by a common envelope or slimy layer, double contoured, and occur singly or in clusters (sori). The morphology of K481-B101 is represented in Table 1.

CULTURAL CHARACTERISTICS

K481-B101 grows moderately on casitone-Mg++agar (McCurdy, 1969) and yeast cell agar (Christensen & Cook, 1978), but poorly on Bacto-nutrient agar or Bacto-heart infusion agar. Rhizoid or feathery swarmings are observed on YP-soft agar (yeast extract 0.3%, peptone 0.1%, NaCl .0.01%, Agar 0.3%, pH 6.6–6:8), but not on casitone-Mg++agar. The colonies on casitone-Mg++agar are circular, translucent and pale greenish yellow, and weakly etch, erode or penetrate into agar. The cultural characteristics are shown in Table 2.

PHYSIOLOGICAL CHARACTERISTICS

K481-B101 hydrolyzes starch, chitin, gelatin and casein, but not cellulose and agar. It lyses autoclaved yeast cell, but not livin cell of *Micrococcus luteus*. K481-B101 is mesophilic, and sensitive to 2% NaCl. The physiological characteristics are shown in Table 3.

CONCOMITANCE OF FLAGELLATE BACTERIA DN OCCURENCE OF SPONTANEOUS VARIANT

Concomitance of Gram-negative, rod-shaped flagellate bacteria was observed in the original culture. K481-B101 was fairly well purified by combining the usual techniques of dilution and single cell isolation with sonication, heat shock treatment or antibiotic sensitivity (e.g. pipemidic acid at 50 mcg/ml) using the myxospore or fruiting body. Unpurified culture of K481-B101-occurred mucoid variants which form whitish dome-shaped colony with swarming halo. The vegetative cells of these mucoid variants are somewhat larger than the parental strain, and measured 0.8–1.0×2.0–3.5 micrometers. The cluster of sporangia (sorus) is predominantly formed by mucoid variants.

TAXONOMIC POSITION

K481-B101 is a fruiting gliding bacterium, isolated from a soil sample. The diagnostic major characteristics of the strain are as follows:

Vegative cells 1) cylindrical, of uniform diameter
2) not tapered at ends
3) penetrable into agar media
4) Congo red, not adsorbed

Myxospores 1) differentiated from vegetative cells
2) oval or spherical
3) non-refractile or refractile

Sporangia 1 sessile
2) oval, spherical or irregular
3) often bounded by a common envelope or slimy layer
4) double contoured
5) pale yellow (lack of distinct color)
6) occurring singly or in clusters (sori)

Cultural and physiological characteristics 1) colony, golden yellow to whitish
2) colonies, weakly etch, erode and penetrate agar
3) chitinolytic but not cellulolytic
4) yeast cell lyzed, but Micrococcus luteus not lyzed The above-mentioned morphological, cultural and physiological characteristics of K481-B101 indicate that K481-B101 is classified into the order Myxobacterales. Among the genera of *Myxobacterales*, the genera *Myxococcus, Archangium* and *Cystobacter* are differentiated from K481-B101 on account of the tapered vegetative cells and the fruiting body morphology. The genera *Melittangium, Stigmatella* and *Chondromyces* differ from K481-B101 in the stalked sporangia.

K481-B10 is similar the Polyangium and Nannocystis. K481-B101 resembles the genus Nannocystis in the formations of oval or spherical myxospores, and oval or spherical, solitary sporangia, but differs from the latter in the cylindrical vegetative cells of uniform diameter and the lack of ability to etch, erode and penetrate into agar. K401-B101 resembles the genus Polyangium in the cylindrical vegetative cells with blunt rounded ends, the predominant formation of non-refractile mysospores and the oval or spherical, double contoured sporangia. Based on the results of comparative studies with the genera of Order Myxobacterales, K481-B101 is considered to be classified as a species of the genus Polyangium. Among the species of Polyangium, *P. luteum* is similar to K4–81-B101 in the size of vegetative cells, the color and shape of s-porangia and the color of vegetative colony. However, K481-B101 differs from *P. luteum* in the oval or spherical myxospores which are much contracted and the lack of ability to lyze bacterial living cells such as the cells of Micrococcus luteus.

Thus, K481-B101 is concluded to be a new species of the genus Polyangium in the family Polyangiaceae, the Order Myxobacterales, and is proposed to be designated *Polyangium* brachysporum sp., nov. The type strain is No. K481-B101 (single isolate), and the culture which has been deposited in the American Type Culture Collection with the accession number 53080.

TABLE 1

| Morphology of K481-B101 | |
| --- | --- |
| Vegetative cells | Gram-negative. Cylindrical with blunt rounded ends. (0.6–0.8 by 2.0–10 micrometers). Congo red, not ad- |

TABLE 1-continued

| | Morphology of K481-B101 |
|---|---|
| | sorbed. |
| Myxospores | Distinguishable from vegetative cells. Much shrunken, becoming oval or spherical, 0.6–0.8 by 0.6–1.5 micrometers, non-refractile. Longer incubation affords refractile ones. |
| Sporangia | Sessile, occurring singly or in clusters. Oval, spherical, pillow-shaped or shapeless. Considerably variable in size, 12 × 20 to 80 × 120 micrometers. Bounded by a common envelope or slimy layer. Double contoured. Embedded in agar. Clusters of two to ten or more sporangia range 50 to 300 micrometers in size of total mass. |
| Microcolony | On chitin agar after incubation for 2 weeks. Palisade or zigzag arrangement of chains of vegetative cells at periphery. Gliding movement of single cells is observed, but that of cell masses is not seen. |

TABLE 2

| Cultural characteristics of K481-B101 Colony on casitone-Mg$^{++}$ agar (McCurdy, 1969) at 28° C. for 6 days | |
|---|---|
| Form | circular |
| Surface | smooth, later partially wrinkled |
| Elevation | raised |
| Edge | entire or somewhat irregular, and absence of distinct protrusion such as shapes of tongue, feather or rhizoid |
| Optical property | semi-transparent or opaque |
| Color of colony | pale greenish yellow |
| Diffusible pigment | none |

Growth on chitin agar after incubation at 28° C. for 3 weeks.

Thin, translucent, pale yellow or colorless. Thick, opaque and yellowis-white at peripheral pat. cocnentric formation of sporangia at the periphery. Weakly etch, erode or penetrate the agar.

TABLE 3

| Physiological characteristics of K481-B101 | |
|---|---|
| Hydrolysis of | |
| Soluble starch | + |
| Potato starch | + |
| CMC sodium | + |
| Cellulose | − |
| Agar | − |
| Chitin | + |
| Alginate sodium | − |
| Polypectate sodium | − |
| Gelatin | + |
| Casein | + |
| Growth on | |
| Simon's citrate agar | − |
| Christensen citrate agar | − |
| Glucose-ammonium salts agar | − |
| Asparagin-ammonium salts agar | + |
| Production of | |
| Indole | − |
| H$_2$S | + |
| Acetoin (VP-reaction) | − |
| Urease | + |
| Oxidase | + |
| Catalase | + |
| Lytic Action to | |
| Living cell of *Micrococcus luteus* strains PCI 1001 & ATCC 9341 | − |
| Autoclaved yeast cell | + |

TABLE 3-continued

| Physiological characteristics of K481-B101 | |
|---|---|
| Reactions | |
| Milk coagulation | − |
| Milk peptonization | + |
| NaCl tolerance | Growth: 1.0% NaCl or less<br>No growth: 2.0% NaCl or more |
| pH tolerance | Growth range: pH 5.5–10.5<br>Scant growth: pH 5.0<br>No growth: pH 4.5 and 11.5 |
| Growth temperature | Maximal growth: 37° C.<br>Growth range: 15° C.–42° C.<br>No growth: 10° C. and 45° C. |
| Oxidative or fermentative reaction | Oxidative (Hugh and Leifson medium) |

ANTIBIOTIC PRODUCTION

The stock culture of *Polyangium brachysporum* K481-B101 was propagated at 28° C for 3 days on agar slant medium composed of 0.5% soluble starch, 0.5% glucose, 0.1% meat extract, 0.1% yeast extract, 0.2% Nz-case, 0.2% NaCl, 0.1% CaCO$_3$ and 1.6% agar (pH 7.0). A well grown algae slant was used to inoculate the vegetative medium consisting of 2% corn starch, 3% soybean meal, 0.3% MgSO$_4$·7H$_2$O and 1% CaCO$_3$ (pH 7.0, before tion). After incubation at 28° C. for 3 days on a rotary shaker (250 rpm), 5 ml of the growth was transferred into a 500-ml Erlenmeyer flask containing 100 ml of the production medium having the same composition as the vegetative medium.

The antibiotic production was monitored by the paper disc agar diffusion method using *Candida albicans* A9540 as the test organism. The fermentation was continued for 4 days at 28° C. on a rotary shaker and the antibiotic production reached a maximum of 100 mcg/ml.

The fermentation was also carried out in a stir-jar fermenter. A 500-ml portion of the seed culture obtained by flask fermentation was used to inoculate 10 liters of the production medium in a 20-liter vessel. The fermentation was carried out at 28° C. with agitation at 250 rpm and aeration at 10 liters per minute. The antibiotic production reached a maximum of 150 mcg/ml after forty hours' fermentation.

ISOLATION AND PURIFICATION OF ANTIBIOTIC

The fermentation broth (48 L) was centrifuged with the aid of a sharpless centrifuge. The gycelial cake was homogenize with 7 L of methanol and the mixture stirred for one hour. After removal of the insolubles by filtration, the methanol extract was evaporated to an aqueous solution which was combined with the broth filtrate and extracted with n-butanol (24 L). The extract was concentrated to 0.5 L which was poured into n-hexane (3.5 L) under stirring to precipitate the crude antibiotic (41 g). This solid was chromatographed on a column of silica gel C-200 (760 ml) eluting with ethyl acetate and an increasing amount of methanol (0–50%). The bioactivity eluted was detected by a paper disc assay using *Candida albicans* A9540 as the test organism. The active fractions were combined and evaporated to yield pale yellow powder (13 g) of BU-2867T complex. A 200 mg-portion of this solid was chromatographed on a reverse-phase column (C$_{18}$, 100 ml) using ethanolwater (3:7 to 5:5) as an eluant. The eluate was monitored by anti-fungal bioassay and TLC (Silanized, EtOH:H$_2$O=55:45). The first active fractions were combined and evaporated under reduced pressure to afford pure white solid of BU-2867T A (61 mg) which was crystallized from aqueous methanol to deposit colorless needles (34 mg). Evaporation of the second and third active fractions yielded BU-2867T B (1 mg) and C (11 mg), respectively. BU-2867T C was crystallized from methanol as fine needles. Repetition of the above reverse-phase chromatography afforded a total of 3.9 g of BU-2867T A, 44 mg of BU-2867T B and 342 mg of BU-2867T C.

CHARACTERIZATION OF ANTIBIOTIC

Figure 1:
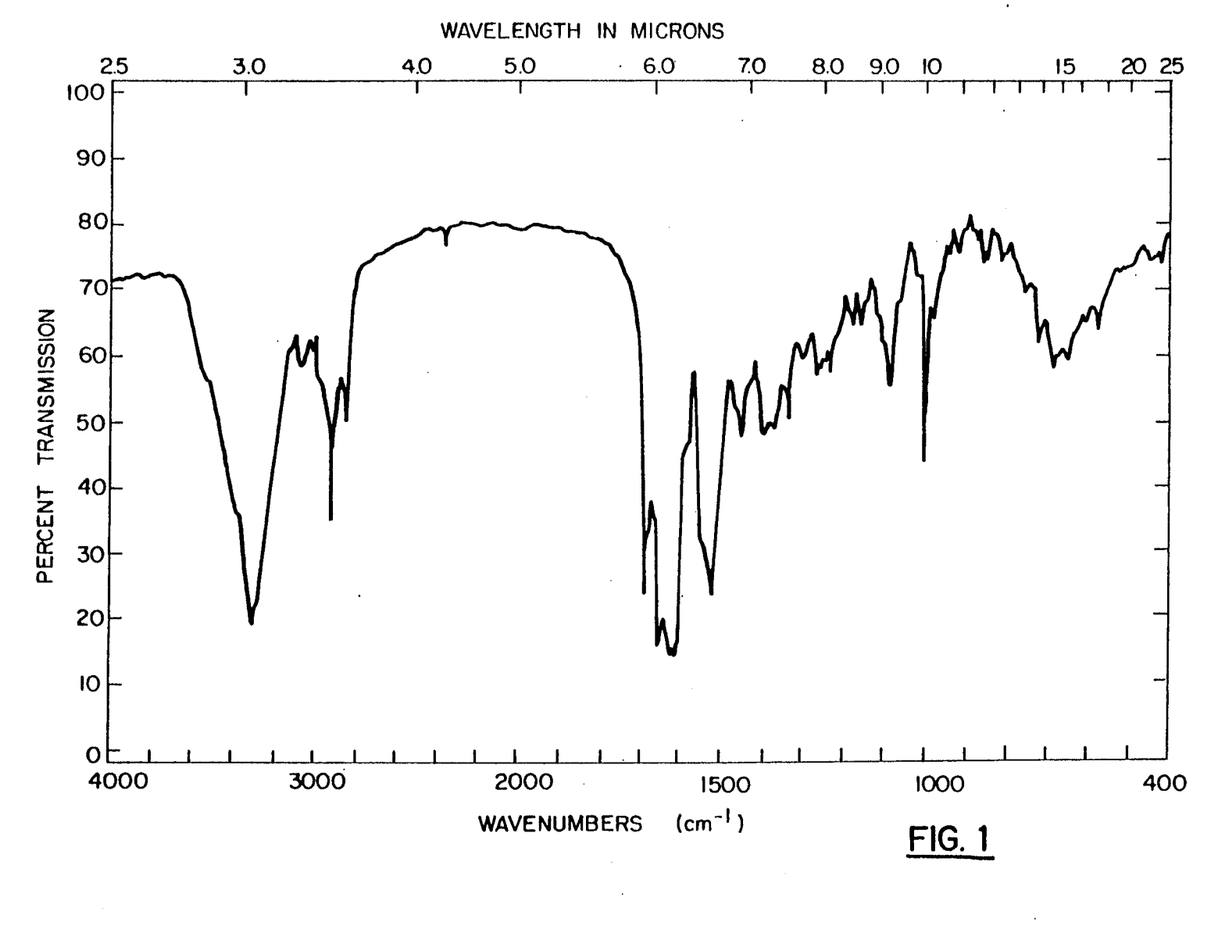
Figure 2:
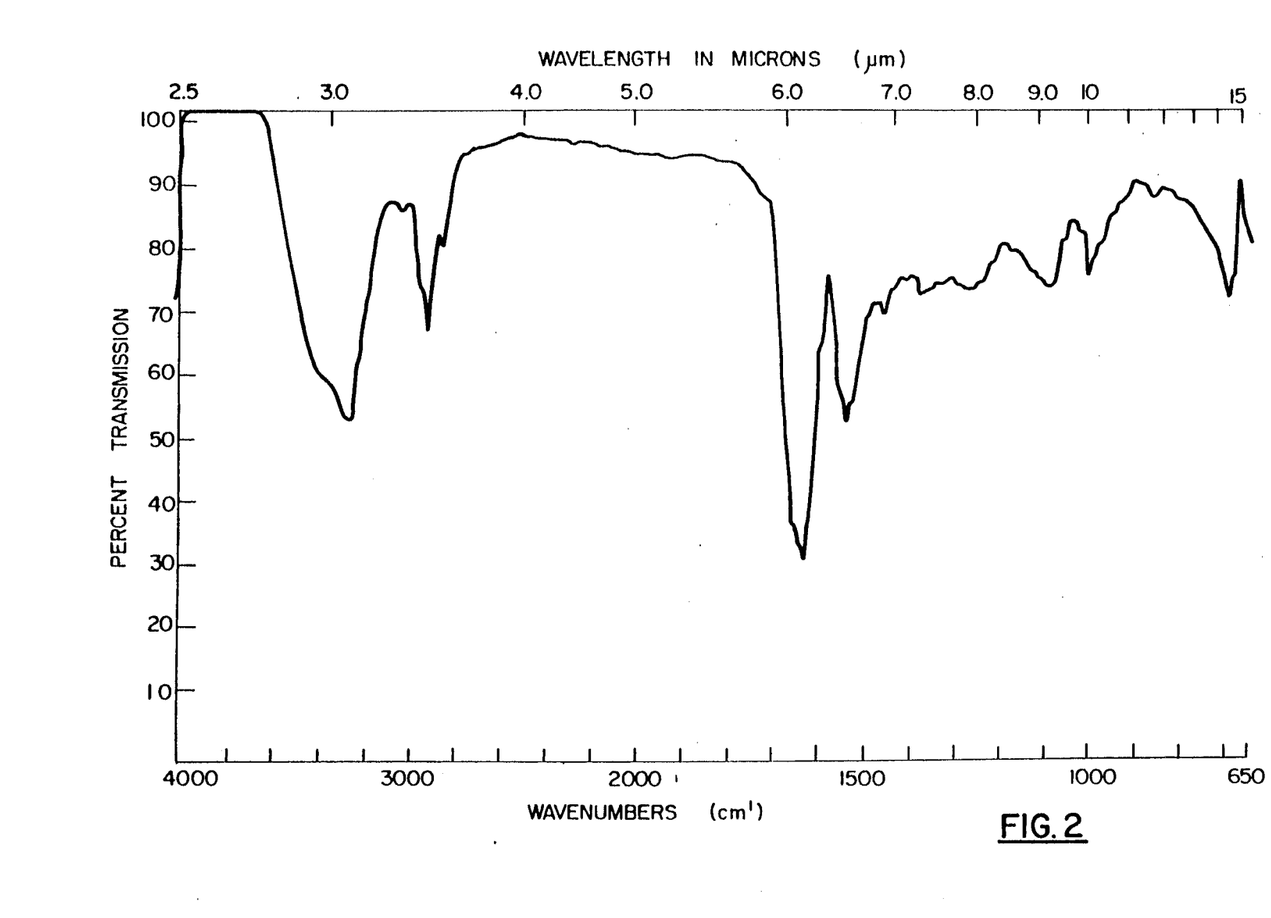
Figure 3:
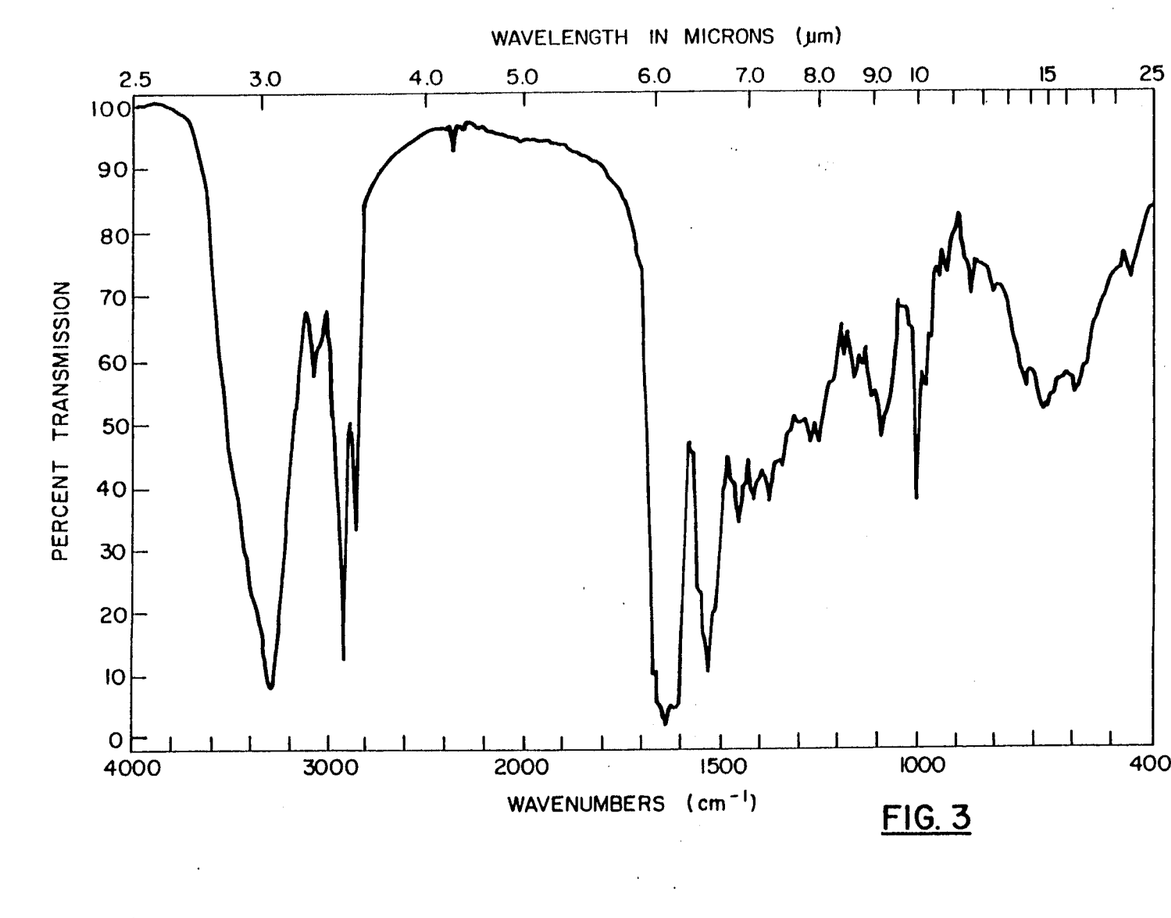
Figure 4:
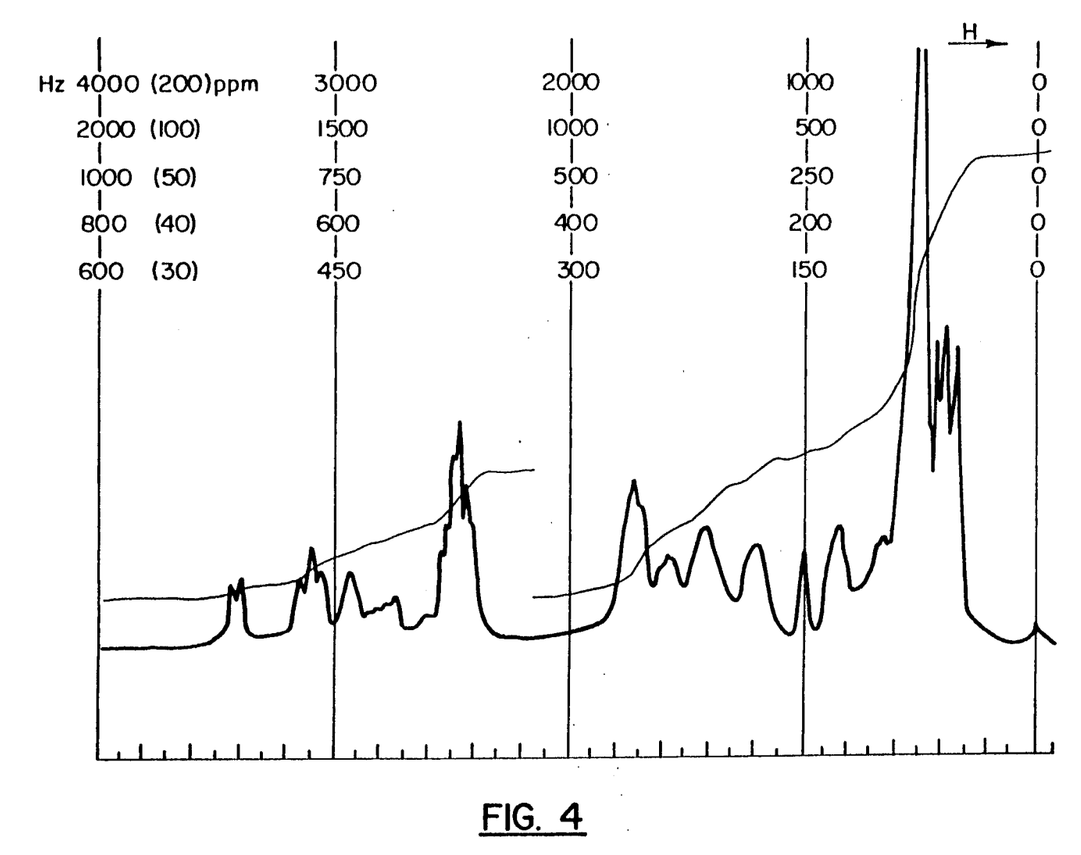
Figure 5:
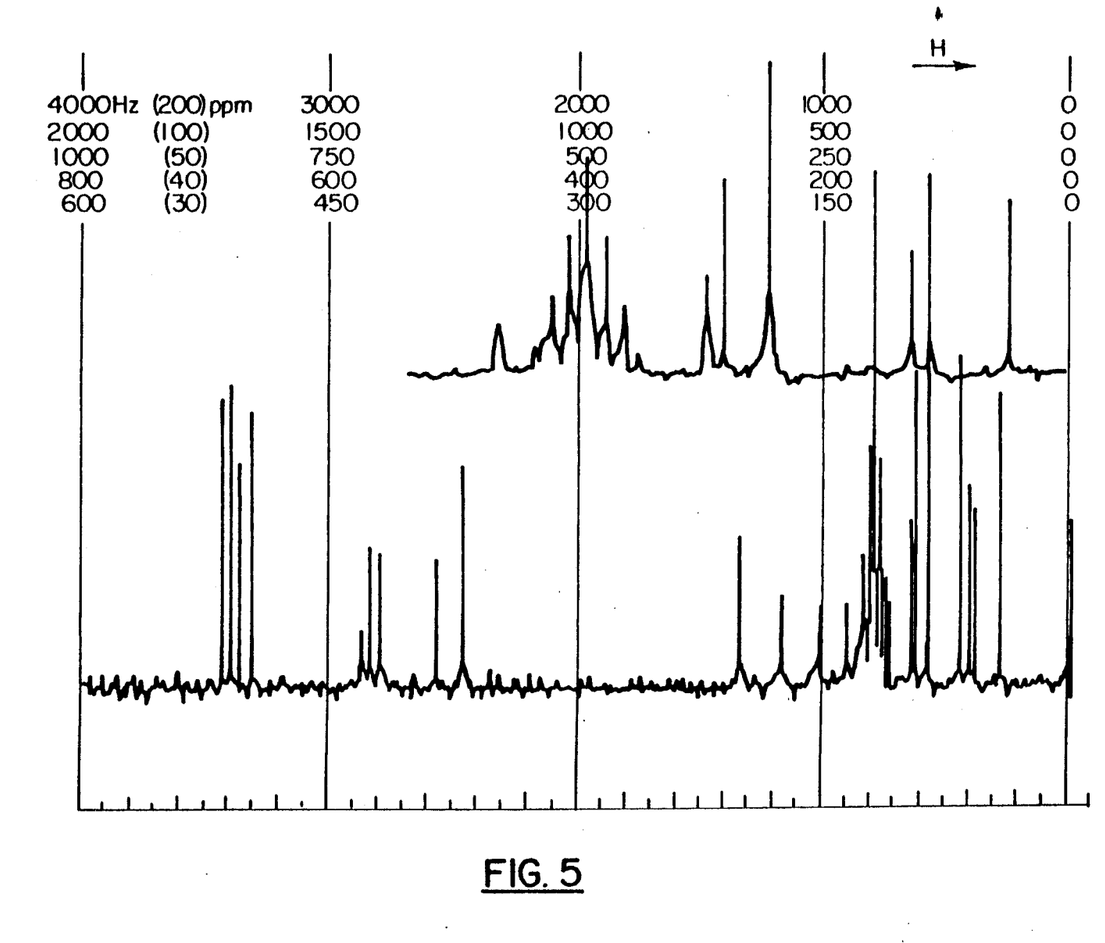

BU-2867T A and C were isolated as colorless needles while BU-2867T B was obtained as white amorphous powder. They are readily soluble in methanol ethanol n-butanol and dimethyl sulfoxide, slightly soluble in choroform, acetonitrile and ethyl acetate and practically insoluble in n-hexane and water. They gave a positive response to Rydon-Smith reagent and colored upon spraying of iodine or sulfuric acid on TLC plate. They were negative to ninhydrin, Sakaguchi, anthrone and Dragendorff reaction. BU-2867T A, B and C were analyzed for $C_{27}H_{44}N_4O_6$, $C_{29}H_{46}N_4O_6$ and $C_{29}H_{48}N_4O_6$, respectively, by the wass spectrometry and incroanalyses. The UV spectra of the three components in methanol exhibited a single maximum at 261 nm, which did not shift in acidic or alkaline solution. The physico-chemical data of BU-2867T A, B and C are summarized in Table 4. Their IR spectra in KBr (FIGS. 1, 2 and 3) showed strong amide bands at around 1630 and 1540 cm$^{-1}$ and OH and/or NH absorption at 3300 cm$^{-1}$. The $^1$H-NMR spectrum of BU-2867T A (FIG. 4) revealed the presence of six olefinic protons ($\delta$:6.16, 6.20 (2H), 6.28, 6.49 and 7.09 ppm) and our amide protons 9, 7.82, 7.87 and 8.72 ppm). Two methyl groups ($\delta$:9.93 ppm, t and 1.07 ppm, d) were also observed in the spectrum. The $^{13}$C-NMR spectrum of BU-2867T A (FIG. 5) showed more than 23 carbon signals including four carbonyl carbons, six olefinic carbons and three methyl carbons. BU-2867T B and C showed the $^{13}$C-NMR spectra very similar to that of BU-2867T A except the presence of two acre olefinic carbons in BU-2867T B and two more methylene carbons in BU-2867T C than in BU-2867T A.

BU-2867T A was heated under reflux with 6N HCl for 16 hours. After removal of the lipophilic product (V) by ethyl acetate extraction the hydrolyzate was concentrated to an oily residue which is chromatographed on Dowex 50W×4 ion-exchange resin by developing with pyridine-formic acid-acetic acid buffer (0.1–0.2M, pH 3.1–5.1). By monitoring with ninhydrin reagent, four amino acids I, II, III and IV eluted in that order were isolated and crystallized as hydrochlorides. Amino acid I ([α]25°: −12.7° in 5N HCl) was identified as L-threo-nine by its physicochemical properties. The $^1$H-NMR spectrum and EI-MS (M+1:m/z 134) of amino acid II indicated that it was a mixture of diastereoisomers of 4-amino-3-hydroxy-n-valeric acid, Konishi, M.; K. Saito, K. Numata, T. Tsuno, K. Asama, H. Tsukiura, T. Naito & H. Kawaguchi : Tallysomycin, a new antibiotic complex related to bleomylin. II. Structure determination of tallysomycins A and B. J. Antibiotics 30: 789–805, 1977, and its identity was confirmed by a direct comparison with the authentic sample. The molecular formula of III was assigned to be $C_5H_9NO_2$ by elemental analysis and EI-mass spectrometry (M+: m/z 115). Its $^1$NMR showed the presence of one methyl ($\delta$:1.50 ppm, d, J:6.0 Hz), one methine ($\delta$:4.0–4.2, m) and two trans olefinic protons ($\delta\delta$:6.05 ppm; d, J:15.0 Hz and 6.57 ppm, d—d, J:6.0 and 15.0 Hz). These spectral data clearly indicated III to 4-amino-2(E)-pentenoic acid, Honore', T.; H. Hjeds, P. Krogsgaard-Larsen & T. R. Christiansen: Synthesis and Structure-Activity Studies of Analogs of γ-amino-butyric Acid (GABA). Eur. J. Med. Chem., 13:429–43–1978. 2(S)-Configuration was assigned to III based on its specific rotation ([α]D$^{22.5}$:−6° in 5N HCl). Amino acid IV was determined to be 4-hydroxylysine based on its elemental analysis ($C_6H_{14}N_2O_3$) EI-MS (M+1:m/z 163) and $^1$H-NMR spectrum ($\delta\delta$:1.8–2.1 ppm 4H, m, 3.18 ppm, 2H, t and 3.6–4.3 ppm, 2H, m) and the formation of a γ-lactone compound ($\nu$C=0 : 1770 cm$^{-1}$) upon treatment with 6N HCl. Izumiya, N.; Y. Fujita, F. Irreverre & B. Witkop: The Synthesis of Erythro-γ-hydroxy-L-lysine and its Nonoccurrence in Collagen. *Biochemistry* 4:2501–2506, 1965, reported mutarotation of 4-hydroxylysines and the shift observed for IV indicated erythro-L-configuration. Thus, the structure of amino acid IV was established to be erythro-4-hydroxy-L-lysine.

The lipophilic acidic fraction (V) obtained in the above acid hydrolysis was treated with diazomethane to yield an oily ethyl ester (VI) after chromatographic purification. Its UV ($\epsilon$MeOH: 260 nm, λ: 22,000), EI-MS (M+: m/z 210) and $^1$H-NMR (four —CH=, one C—CH$_3$ and sie —CH$_2$—) indicated that V was methyl 2,4-dodecadienoate. The magnitude of coupling constant made it obvious that both double bonds had a trans geometry. The original acid V was thus 2(E), 4(E)-dodecadienoic acid, Burden, R. S. & L. Crombie: Amides of Vegetable Origin, Part XII. A new series of alka-2,4-dienoic tyramine-amides from *Anacyclus pyrethrum* D.C. (*Compositae*). *J. Chem. Soc.* (C), 1969: 2477–2481, 1969.

I: L-Threonine

II: 4-Amino-3-hydroxy-n-valeric acid

III: 4(S)-Amino-2(E)-pentenoic acid

IV: ERYTHRO-4-hydroxy-L-lysine

| | -continued | |
|---|---|---|
| V: 2(E),4(E)-Dodecadienoic acid | $CH_3-(CH_2)_6-CH=CH-CH=CH-COOH$ | |

BU-2867T A has the molecular formula of C and showed six olefinic carbons and four amide carbons in the $^{13}$C-NMR. It was therefore apparent that amino acid II was an artifact produced by hydration of the natural amino acid III during acid hydrolysis. The antibiotic should be a cyclic peptide since it was negative to ninhydrin reaction and did not exhibit any titratable function in potentiometric titration. This was further supported by a fact that BU-2867T A afforded a di-O-acetyl drviattive (EI-MS:M$^+$ = m/z 604,$^1$H-NMR: 2.02 ppm, 3H and 2.08 ppm, 3H) upon acetylation in pyridine. .The MS of the acetate also indicated strong.fragment ions at m/z 179 and 322 which suggested the presence of V→I→ sequence in the antibiotic.

BU-2867T A was subjected to enzymatic degradation with ficin in 0.01M phosphate buffer (pH 7.0). After being acidified to pH 2.2, the reaction mixture was extracted with n-butanol to obtain an acidic compound (VII). Subsequent extraction of the aqueous solution at pH 10.0 with n-butanol afforded a ninhydri-positive substance (VIII). Compound VII was shown to be 2,4-dodecadienoyl-threonine (V→I) by the IR($^{84}C=O$:1720 & 1650 cm$^{-1}$), EI—MS(M$^+$—H$_2$O:m/z 279 and M$^+$—Thr : m/z 179) and $^1$H-NMR spectrum. The structure was further substantiated by the facts that VII yielded I and V on hydrolysis in 6N HCl. When refluxed in 6N HCl, compound VIII afforded amino acids II, III and IV as revealed by TLC. In the EI—MS of VIII, the molecular ion was found at m/z 241 indicating a cyclic peptide structure. The $^1$H-NMR (270 MHz, in DMSO-d$_6$) exhibited two amide NH protons at: 7.43 (triplet) and 9.10 ppm (broad) in agreement with the above cyclic structure. Extensive decoupling experiment revealed that the amino group of III and α-amino group of IV were linked to carbonyls to form amides while α-amino group of IV was free. Thus, the structure of VII and VIII were assigned as shown below:

$$CH_3-(CH_2)_6-CH\overset{E}{=}CH-CH\overset{E}{=}CH-CO-NH-\underset{|}{CH}-COOH \quad \text{VII}$$
$$\overset{CH_3}{\underset{CHOH}{|}}$$

VIII

Compounds VII and VIII were also obtained when BU-2867T A was subjected to enzymatic degradation or hydrolysis with papain or chymopapain. A mixture of BU-2867T A (4 g) and papain (Sigma P-3375, 50 g) in 20 L of 10% aqueous methanol was stirred at 28° C. for 22 hours. The mixture was then acidified to pH 3.3 by acetic acid and extracted with ethyl acetate (10 L). Evaporation of the extract afforded an oil (6.3 g) which was chromatographed of silica gel (Wakogel C-200, 250 ml) with a mixture of CH$_2$Cl$_2$ and methanol (9:1) to give a semi-pure, oily compound VII (3.3 9). Further chromatography of the oil by Sephadex LH-20 and subsequent crystallization gave colorless needles of pure VII. (yield 50%). M.p. 90°–91° C. $[\alpha]^{27}_D$+17.4° (C 0.5, MeOH), Anal. Calcd. for $C_{16}H_{27}NO_4\cdot H_2O$ : C 60.93, H 9.27, N 4.44. Found: C 61.34 H 9.03, N 4.20. EI-MS: m/z 279 (M$^+$—H$_2$O). UV $\epsilon^{MeOH}$max nm (λ): 260 (28,000). IR $\nu$max(KBr) cm$^{-1}$: 3520, 3410, 3300, 1720, 1690, 1655, 1630, etc. $^1$H-NMR (80 MHz, DMSO-d$_6$)δ0.88 (3H, t), 1.06 (3H, d), 6.20 (3H, m), 7.00 ($^1$H, m), 7.84 ($^1$H, d, NH), etc.

After ethyl acetate extraction, the acidic aqueous solution was concentrated to dryness. The residue (36 g) was dissolved in 50 ml of water, adjusted to pH 9.0 and applied on a column of reverse phase silica (C$_{18}$, Merck, 1.6 L) which was developed with water. The fractions containing compound VIII were pooled and concentrated in vacuo. The residue was chromatographed on Sephadex LH-20 (250 ml) with 50% aqueous methanol and then on reverse phase silica (C$_{18}$) with acidic water (pH 3.0 by dil HCl) afforded pure VIII hydrochloride. 747 mg (yield 35%). M.p. 190° C. (dec.). :$[\alpha]^{26}_D$−113° (c 0.5, H$_2$O). EI-MS : m/z 241 (M$^+$). UV: end absorption. IR $\nu_{max}$ (KBr) cm$^{-1}$: 3400, 1660, 1620, 1530, etc. $^1$H-NMR (80 MHz, DMSO-d$_6$) δ6 1.27 (3H, d), 1.4–1.8 (4H), 2.98 (2H, m), 4.52 (1H, m), 6.19 ($^1$H, d), 6.45 ($^1$H, d—d), 7.43 ($^1$H, t, NH), 9.46 (1H, d, NH). Analysis Calcd for $C_{11}H_9N_3O_3\cdot HCl\cdot H_2$: C 44.67, H 7.50, N 14.21, Cl 11.99. Found: C 45.04, H 7.82, N 13.81, Cl 12.55.

Since BU-2867T A was negative to ninhydrin and did not exhibit any titratable group, its structure was logically that constructed by linking VII and VIII by a peptide bond.

On heating with 6N HCl, both BU-2867T B and C afforded the same amino acid complex as that obtained from BU-2867T A. The fatty acid moieties cf the two antibiotics were extracted from the hydrolyzate, treated with diazomethane and isolated as methyl esters, IX (from BU-2867T B) and X (from BU-2867T C). They retained the characteristic UV maximum ($\lambda^{MeOH}_{max}$ : 260 nm) observed for their parent antibiotics. The EI-MS of IX yielded a molecular ion at m/z 236, suggesting a C$_{14}$-acid ester having three double bonds. The UV and $^1$H-NMR spectra distinctly showed 2(E), 4(E)-dienoic acid structure and the third double bond to be isolated in IX. Ozonolysis of IX followed by reductive degradation of the ozonide yielded n-hexanal which was isolated and identified as 2,4-dinitrophenyl-hydrazone (EI—MS M$^+$: m/z 280). These evidences established that IX weight of ester X (EI—MS ; M$^+$m/z 238) was found to be 28 units (C$_2$H$_4$) higher than that of VI reflecting the molecular formula difference observed between BU-2867T A and C. This combined with the $^1$H-NMR and UV data, revealed X to be methyl 2(E), 4(E)-tetradecadienoate. The results of the above experiments indicated the following structures for BU-2867T A, B and C:

BU-2867T A: R = CH$_3$—(CH$_2$)$_6$—
BU-2867T B: R = CH$_3$—(CH$_2$)$_4$—CH=CH—(CH$_2$)$_2$—
BU-2867T C: R = CH$_3$—(CH$_2$)$_8$—

TABLE 4

| | Physico-chemical Properties of BU-2867T A, B and C | | |
|---|---|---|---|
| | BU-2867T A | BU-2867T B | BU-2867T C |
| Nature | Colorless needles | White powder | Colorless needles |
| M.p. | 259–261° C. | 232–234° C. | 273–275° C. |
| $[\alpha]_D^{24°}$ (c 0.5 MeOH) | −111° | −92° | −104° |
| Microanalysis: | | | |
| Calcd for | C$_{27}$H$_{44}$N$_4$O$_6$·½H$_2$O | C$_{29}$H$_{46}$N$_4$O$_6$·3/2H$_2$O | C$_{29}$H$_{48}$N$_4$O$_6$ |
| Found | C 61.22, H 8.56, N 10.58 | C 60.71, H 8.61, N 9.77 | C 63.48, H 8.82, N 10.21 |
| | C 60.90, H 8.65, N 10.47 | C 60.89, H 8.31, N 9.23 | C 63.48, H 8.91, N 10.16 |
| EI-MS m/z | 520 (M$^+$) | 546 (M$^+$) | 548 (M$^+$) |
| UV $\lambda_{max}^{MeOH}$ nm ($\epsilon$) | 261 (35,000) | 261 (28,000) | 261 (36,000) |
| TLC Silanized plate Rf EtOH—H$_2$O (55:45) | 0.45 | 0.41 | 0.34 |
| HPLC Lichrosorb Rp-18 Rt EtOH—H$_2$O (65:35) | 6.43 | 7.93 | 11.33 |

Enzymatic degradation of BU-2867T with Pseudomonas acylase gave different products than those obtained by hydrolysis with ficin or papain described above. Pseudomonas strain Pa-129 was fermented in 10 L of medium containing 2% soluble starch, 0.2% glucose, 3% soybean meal, 1% CaCO$_3$ and 0.3% MgSO$_4$·7H$_2$O at 37° C. for 3 days and the cells were collected by centrifugation. After being washed with saline (1 L) two times, the cells were resuspended in 0.75 L of saline. The cell suspension was mixed with pre-autoclaved suspension (1.5 L) of sodium alginate (75 g) and CM-cellulose (75 9) and the mixture poured into 30 L of 0.1M CaCl$_2$ solution under stirring. The 9e-1 entrapped in the cells was stiffened by stirring with 25% glutaraldehyde solution and packed in a column (4.0×175 cm). A solution of BU-2867T A (1.5 g) in 20% aqueous methanol (30 L) was passed through the column at a flow rate of 0.4–0.8 L/hour. The pooled effluent was then passed through an Amberlite IRC-50 (70% NH$_4$$^+$ form, pH 6.7, 300 ml) and HP-20 column (300 ml) successively. The IRC-50 column was washed with water and then developed with 1.5 N NH$_4$OH. The ninhydrin positive fractions were pooled, concentrated and lyophilized to give pale yellow solid (800 mg) which was charged on a column of reverse phase silica (C$_{18}$, 250 ml). The column was developed with water under medium-pressure and the ninhydrin-positive eluates were pooled and concentrated to yield white solid of L-threonylcyclic amine (XI, 612 mg). Yield 62%. M.p. 170° C., $[\alpha]^{27}_D$−157° (c 0.5, H$_2$O). EI-MS: m/z 342 (M$^+$).UV: end adsorption. IR$\nu_{max}$ (KBr) cm$^{-1}$: 3350, 3280, 1650, 1620, 1530 etc. $^1$H-NMR (80 MH$_z$, DMSO—d$_6$) δ1.05 (3H, d), 1.21 (3H, d), 1.4–2.2 (4H), 4.35 (2H, m), 4.47 ($^1$H, m, OH), 4.62 ($^1$H, d, OH), 6.16 (1H, d), 6.42 (1H, d—d), 7.36 (1H, t, NH), 7.97 (1H, d, NH), 8.62 (1H, d, NH).

XI: CH$_3$—CH—CH—CO—NH—
         |    |
         OH  NH$_2$

The HP-20 column obtained above was developed with water (1 L) and then a mixture of 0.1N NaOH and methanol (1:2). Fractions containing 2,4-dodecadienoic acid (V) were pooled, concentrated to 300 ml and acidified to pH 2.0. This solution was extracted with ethyl acetate (300 ml) and n-butanol (100 ml). Evaporation of the ethyl acetate extract gave an oily residue which was chromatographed on a columr of Sephadex LH-20 (800 ml). Upon elution with methanol and monitoring the eluates by UV absorption at 260 nm, the appropriate eluates were concentrated to yield colorless plates of pure V (259 mg). Yield 53%. M.p. 48°–49° C. UV $\lambda^{MeOH}_{max}$ nm ($v$) : 258 (24,000). IR U$_{max}$(KBr) cm$^{-1}$: 1680, 1630, 1605, 1410, 1300 etc. $^1$H-NMR (80MHz, CD$_3$OD) δ0.89 (3H, t), 2.0 (10H), 2.12 (2H, m); 5.75 (1H, d), 6.16 (2H, ml, 7.21 (1H, m). This compound was identical with 2,4-dodecadienoic acid obtained by acid hydrolysis of BU-2867T A. The n-butanol extract was concentrated in vacuo and lyophilized to recover the starting material, BU-2867T A (160 mg, 11%).

It is apparent from the discussion above that compounds VIII and XI are valuable intermediates useful in preparing the various antibiotic compounds of the present invention. Conventional acylation, for example, with a mixed anhydride of a carboxylic acid with an alkyl acid carbonate (HOCOOR) forms the requisite peptide bond, *Advanced Organic Chemistry*, Fieser & Fieser, pages 1039–1046, Reinhold Publishing Corporation, N.Y. 1965. Hydroxyl groups may be protected in any convenient manner for example, as the tetrahydropyranyl or t-butyl ethers. Acylation of the amine group of VIII with the acids and yields BU-2867T A, B and C, respectively. For example, BU-2867T is prepared by the coupling of VII and VIII. A mixture of VII (15 mg), N,N'-dicyclohexyl odiimide (10 mg) and 1-hydroxy-2,3-benzotriazole (8 mg) in 2 ml of dimethylformamide was stirred for two hours at room temperature. Compound VIII (10 mg) was then added to the mixture and stirring continued overnight. The solution was concentrated to a residue which was chromatographed on reverse phase silica, ($C_{18}$, 40 ml) with 80% methanol elution. The active eluates were evaporated and the residue was purified by preparative HPLC (column: SSD-ODS-842, mobile phase: 90% aqueous methanol). Evaporation of the active peak fraction gave BU-2867T A (7.4 mg, yield 28%) which was identical in all respects with the natural antibiotic. TLC (Silanized, EtOH—$H_2O$=55:45) Rf: 0.45. HPLC (Lichrosorb RP-18, EtOH—$H_2O$=65:35) Rt: 6.43 min.

BU-2867T A can also be prepared by coupling with XI. A dimethylformamide solution (1 ml) of V (3.4 mg), N,N'-dicyclohexylcarbodiimide (3.7 mg) and 1-hydroxy-1,2,3-benzotriazole (2.8 mg) was stirred for 2 hours at room temperature. To the solution was added XI (5 mg) and the mixture kept stirring for additional 3 hours and concentrated in vacuo. The residue was dissolved in methanol and purified by preparative HPLC using the same column and mobile phase as described above. BU-2867T A 4 mg, yield 45%. Identity with natural BU-2867T A was confirmed by a direct comparison.

Compound XI can be prepared from Compound VIII using conventional procedures. To a stirred mixture of N-t-butoxy-carbonyl-L-threonine (44 mg), N,N'-dicyclohexylcarbodiimide (40 mg) and 1-hydroxy-1,2,3-benzotriazole (30 mg) in dimethyl-formamide (4 ml) was added VIII (40 mg) at room temperature. The mixture was concentrated in vacuo to a residue which was chromatographed on a column of reverse phase silica ($C_{18}$, 40 ml) with methanol and water mixture (ratios: 1:9 to 2:3). The appropriate fractions were pooled, concentrated in vacuo and lyophilized to yield N-BOC-L-threonyl-VIII (=BOC-XI). 51 mg Yield, 69% $\nu^{KBr}_{c=o}$:1690 and 1640 cm$^{-1}$. $^1$H-NMR (80 MHz) $\nu_{ppm}$ in $DMSOd_6$: 1.00 (3H, d), 1.22 (3H, d), 1.35 (9H, s), 6.11 ($^1$H, d), 6 33 (1H, d—d), etc. A mixture of BOC-XI (36 mg) and formic acid (1 ml) was stirred for 1 hour at room temperature. This was concentrated, diluted with water (1 ml), adjusted pH 10.0 and applied to a column of reverse phase silica, 20 ml). Upon developing with water and monitoring the eluate with ninhydrin test, the appropriate eluates were combined and freeze-dried to give white solid of XI. 25 mg Yield 88%. $\nu^{KBr}_{c=o}$: 1650cm$^{-1}$. $^1$H-NMR $\delta_{ppm}$ in DMSO-$d_6$: 1.04 (3H, d), 1.22 (3H, d), 6:14 ($^1$H, d), 6.42 (1H, d—d), 7.35 (1H, t, NH), 7.98 (1H, d, NH), 8.65 (1H, d, NH) etc. EI-MS: M+m/z 342.

Thus it is possible to prepare the antibiotic compounds of the invention by reaction of compounds VIII and XI with the appropriate acids, whatever their source. Further, using compounds VIII and XI, compounds according to the invention, particularly those produced in higher yields, can be used to prepare other compounds of the invention. For example, BU-2867T A, which is obtained in higher yields by fermentation, can be used to prepare BU-2867T B and BU-2867T C, by enzymatic hydrolysis and coupling with the desired acid, as illustrated above.

The yield of BU-2867T and the distribution of the A, B and C fractions obtained by fermentation, as described above, can be modified by adding various fats and oils and certain surface active agents the medium in which *Polyangium brachysporum* K481-B101 is being cultivated. For example, the addition of soybean oil, corn oil, olive oil, hydrogenated vegetable oil, lard and tallow to a lesser extent, increased the total yield of BU-2867T obtained. Fats and oils having a high content of linoleic acid ($C_{18:2}$), such as soybean oil, corn oil and lard,-led to an increase in the preparation of BU-2867T B formed. Oils, such as olive oil, having a high content of oleic acid ($C_{18:1}$) led to an increase in the proportion of BU-2867T C formed. Hydrogenated vegetable oils rich in stearic acid ($C_{18:0}$) only increased the amount of BU-2867T A formed.

Antimicrobial Activity

The minimum inhibitory concentrations (MICs) of BU-2867T A, B and C were determined for various microorganism by a serial agar dilution method. Nutrient agar (Eiken) was used for bacteria and Sabouraud dextrose agar (Difco) for fungi. The inoculum size was adjusted to $10^4$ CFU/ml for bacteria and $10^5$-$10^7$ CFU/ml for fungi.

Table 5 shows in vitro antibacterial activities of BU-2867T A, B and C. Components A and C did not inhibit the growth of both gram-positive and gram-negative bacteria at 50 mcg/ml, while component B showed moderate activity against some gram-positive bacteria.

The antifungal activities of BU-2867T components are shown in Table 6. Components C showed potent antifungal activity against clinically important pathogenic fungi such as *Candida albicans, Cryptococcus neoformans, Asergillus fumigatus, Trichophyton mentarophytes* and *Mucor spinosus.* Components A and B were somewhat less active than component C, but their antifungal spectra were similar to that of the latter.

TABLE 5
Antibacterial Spectra of BU-2867T Components

| | | MIC (mcg/ml) | | |
|---|---|---|---|---|
| | | BU-2867TA | BU-2867B | BU-2867C |
| Gram-positive Organism | | | | |
| Staphylococcus aureus | 209P | >50 | 25 | >50 |
| Staphylococcus aureus | Smith | >50 | 3.1 | >50 |
| Staphylococcus aureus | Bx-1633 | >50 | 50 | >50 |
| Staphylococcus epidermidis | D153 | >50 | 6.3 | >50 |
| Staphylococcus epidermidis | A22152 | >50 | 50 | >50 |
| Streptococcus faecalis | A9612 | >50 | >50 | >50 |
| Micrococcus luteus | PCI-1001 | >50 | 50 | >50 |
| Bacillus subtilis | PCI-219 | >50 | 50 | >50 |
| Gram-negative Organism | | | | |
| Escherichia coli | NIHJ | >50 | >50 | >50 |
| Klebsiella pneumoniae | D-11 | >50 | >50 | >50 |
| Proteus mirabilis | A9554 | >50 | >50 | >50 |
| Proteus vulgaris | A9436 | >50 | >50 | >50 |
| Morganella morganii | A9553 | >50 | >50 | >50 |
| Serratia marcescens | A20222 | >50 | >50 | >50 |
| Enterobacter cloacae | A9659 | >50 | >50 | >50 |
| Pseudomonas aeruginosa | A9930 | >50 | >50 | >50 |

Medium: Nutrient agar

TABLE 6
Antifungal Spectra of BU-2867 T Components

| | | MIC (mcg/ml) | | |
|---|---|---|---|---|
| Test organism | | BU-2867A | BU-2867B | BU-2867C |
| Candida albicans | IAM 4888 | 3.1 | 3.1 | 1.6 |
| Candida albicans | A 9540 | 1.6 | 1.6 | 0.8 |
| Cryptococcus neoformans | D 49 | 25 | 25 | 3.1 |
| Cryptococcus neoformans | IAM 4514 | 25 | 25 | 3.1 |
| Aspergillus fumigatus | IAM 2530 | 1.6 | 3.1 | 0.8 |
| Aspergillus fumigatus | IAM 2034 | 1.6 | 3.1 | 0.8 |
| Aspergillus flavus | FA 21436 | 25 | 25 | 50 |
| Fusarium moniliforme | A 2284 | >50 | >50 | >50 |
| Piricularia oryzae | D 91 | >50 | >50 | >50 |
| Trichophyton mentagrophytes | D 155 | 25 | 12.5 | 1.6 |
| Trichophyton mentagrophytes | #4329 | 25 | 12.5 | 6.3 |
| Blastomyces dermaditis | IFO 8144 | 50 | 50 | >50 |
| Sporothrix schenckii | IFO 8158 | >50 | >50 | >50 |
| Petriellidium boydii | IFO 8073 | >50 | >50 | 50 |
| Mucor spinosus | IFO 5317 | 1.6 | 0.8 | 0.2 |

Medium: Sabouraud dextrose agar

Antitumor activity

The antitumor activity of BU-2867T A, B and C was determined in female $CDF_1$ and male $BDF_1$ mice. Lymphocytic leukemia P388 ($CDF_1$ and $BDF_1$ mice) and lymphoid leukemia L1210 ($BDF_1$ mice) were inoculated by intraperitoneal injection of 0.8 ml diluted ascitic fluid containing $10^6$ and $10^5$ cells per mouse, respectively. Melanotic melanoma B16 ($BDF_1$ mice) were implanted 0.5 of a 10% tumor brei intraperitoneally. Test materials were dissolved in 0.9% saline containing 10% dimethyl sulfoxide and graded doses of them were administered to mice intraperitoneally 24 hours after tumor implantation. Either olivomycier (NSC 38270) or mitomycin C was comparatively tested as a reference compound in the experiments.

BU-2867T A, B and C showed antitumor activity against P388 leukemia by the treatment schedule 1 (once daily on days 1, 4 and 7). Table 7 shows the results obtained as the increase in median survival time (MST) of test (T) and control (C) animals for various dosage regimens expressed as a percentage ratio. Values for percentage ratios of 125 and above indicate significant antitumor effect.

TABLE 7
Antitumor Activity of BU-2867T Components Against P388 Leukemia

| | T/C % of MST Dose in mg/kg/day, ip | | | |
|---|---|---|---|---|
| | 3 | 1 | 0.3 | 0.1 |
| BU-2867T A | | 140 | 130 | 120 |
| BU-2867T B | 165 | 140 | 120 | |
| BU-2867T C | 155 | | 130 | |
| Olivomycin A | 140 | 135 | 100 | |

BU-2867T A and C were highly active against P388 leukemia by the treatment schedule 2 (once daily on days 1 through 9); BU-2867T A was less active against L1210 leukemia and B16 melanoma. Table 8 shows the results obtained for various schedule dosage regimens again expressed as a percentage ratio increase in median survival time, with values of 125 and above indicating significant antitumor effect.

TABLE 8
Antitumor Activity of BU-2867T A and C

| | T/C % of MST Dose in mg/kg/day. ip | | | | | | |
|---|---|---|---|---|---|---|---|
| | 2 | 1 | 0.5 | 0.25 | 0.13 | 0.063 | 0.031 |
| P388 leukemia | | | | | | | |
| BU-2867T A | 67 | 228 | 186 | 156 | 147 | 136 | 109 |
| BU-2867T C | 234 | 189 | 175 | 159 | 153 | 123 | 100 |
| Mitomycin C | | 290 | 240 | 170 | 150 | 130 | 115 |
| L1210 leukemia | | | | | | | |
| BU-2867T A | | | 129 | 118 | 118 | 106 | |
| Mitomycin C | | 140 | 141 | 129 | 129 | 106 | |
| B16 melanoma | | | | | | | |
| BU-2867T A | Tox. | 125 | 116 | 113 | 100 | | |
| Mitomycin C | 63 | 181 | 163 | 141 | 131 | | |

The acute toxicity of BU-2867T A and C was determined in male ddY mice by single intraperitoneal administration. The $LD_{50}$ values were 8.1 mg/kg and 25 mg/kg, respectively.

The pharmacologically effective compounds of this invention can be processed by conventional methods of galenic pharmacy into pharmaceutical -preparations for oral or parenteral administration, e.g., to mamals including humans. Conventional excipients are pharmaceutically acceptable organic o inorganic carrier substance suitable for parenteral, enteral or topical application which do not deleteriously react with the active compounds. Suitable pharmaceutically acceptable carriers include, but are not limited to, water, salt solutions, alcohols, gum arabic, vegetable oils, polyethylene glycols, gelatin, lactose, amylose, magnesium stearate, talc, silicic acid, petrolatum, perfume oil, fatty acid monoglycerides and diglycerides, pentaerythritol fatty acid esters, hydroxy-methylcellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or inplants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by mlcroencapsulation, multiple coatings, etc.

Generally the compounds of this invention are dispensed in unit dosage form in a pharmaceutically acceptable carrier comprising the requisite dosage The dosage of the compounds according to this invention generally is 5-250 mg/day when administered to patients, e.g., humans weighing 75 kg. Suitable dosages and regimens for a given host can be determined using conventional considerations, e.g., by customary comparison of the differential activities of the subject compound and of a known antibiotic or antitumor agent, e.g., by means of an appropriate, conventional pharmacological protocol.

From the foregoing description, one skilled in the art can readily ascertain the essential characteristics of this invention, and without departing from the spirit and scope thereof, can make various changes and modifications of the invention to adapt it to various usages and conditions.

What is claimed is:

1. A method of the preparation of a compound of the formula which comprises hydrolyzing a compound of the formula wherein R is $CH_3—(CH_2)_6$, $CH_3—(CH_2)_4—CH=CH—(CH_2)_2$, or $CH_3—(CH_2)_8$, in the presence of ficin, papain or chymopapain.

2. A method or the preparation of a compound of the formula which comprises hydrolyzing a compound of the formula wherein R is $CH_3—(CH_2)_6$, $CH_3—(CH_2)_4—CH=CH—(CH_2)_2$ or $CH_3—(CH_2)_8$, in the presence of Pseudomonas acylase.

* * * * *